United States Patent [19]

Michaels

[11] 4,455,144
[45] Jun. 19, 1984

[54] DISPENSER CONSTRUCTED WITH SEMIPERMEABLE POLYMER-HYDROPHILIC POLYMER WALL

[75] Inventor: Alan S. Michaels, San Francisco, Calif.

[73] Assignee: ALZA Corporation, Palo Alto, Calif.

[21] Appl. No.: 424,095

[22] Filed: Sep. 27, 1982

Related U.S. Application Data

[63] Continuation of Ser. No. 212,815, Dec. 4, 1980, abandoned.

[51] Int. Cl.³ ............................................. A61M 7/00
[52] U.S. Cl. ..................................... 604/892; 604/891
[58] Field of Search ............................ 604/890–892, 604/896–897, 304–305, 307–308

[56] References Cited

U.S. PATENT DOCUMENTS

| 3,865,108 | 2/1975 | Hartop | 128/260 |
| 3,987,790 | 10/1976 | Eckenhoff et al. | 128/260 |
| 4,058,124 | 11/1977 | Yen et al. | 128/284 |
| 4,105,033 | 8/1978 | Chatterjee et al. | 128/285 |
| 4,116,241 | 9/1978 | Theeuwes et al. | 128/260 |
| 4,180,073 | 12/1979 | Michaels | 128/260 |
| 4,203,440 | 5/1980 | Theeuwes | 128/260 |
| 4,203,441 | 5/1980 | Theeuwes | 128/260 |
| 4,304,232 | 12/1981 | Michaels | 604/891 |

Primary Examiner—C. Fred Rosenbaum
Assistant Examiner—Sherri E. Vinyard
Attorney, Agent, or Firm—Paul L. Sabatine; Edward L. Mandell

[57] ABSTRACT

A dispenser is disclosed comprising a housing formed of a semipermeable polymer having a hydrophilic polymer grafted thereto. The housing surrounds a container made of an elastomeric material and the container has an outlet through the housing to the exterior of the dispenser.

10 Claims, 3 Drawing Figures

DISPENSER CONSTRUCTED WITH SEMIPERMEABLE POLYMER-HYDROPHILIC POLYMER WALL

CROSS REFERENCE TO RELATED APPLICATION

This application is a continuation of U.S. patent application Ser. No. 06/212,815 filed on Dec. 4, 1980, now abandoned.

FIELD OF THE INVENTION

This invention pertains to a dispenser constructed with a wall comprising a semipermeable polymer having a hydrophilic polymer grafted thereto. The dispenser is useful for delivering fluids and beneficial agents to environments of use.

BACKGROUND OF THE INVENTION

Dispensers are used in commerce and science for delivering fluids and beneficial agents to many varied and diverse environments of use. For example, patentee Theeuwes in U.S. Pat. No. 3,760,984 discloses a dispenser useful for these purposes. The dispenser comprises a chamber formed of a shrinkable polymer carrying on its outer surface a layer of an osmotic solute and a distant layer of a semipermeable polymer. The dispenser has a means for filling the chamber. The dispenser delivers its contents by imbibing fluid into the dispenser, wherein the fluid dissolves the solute and forms a solution, which solution exerts pressure against the chamber, causing it to shrink and deliver its contents from the dispenser. Another dispenser is disclosed in U.S. Pat. No. 3,865,108 by patentee Hartop. The Hartop patent describes a dispenser that comprises components arranged concentrically and consisting of an inner collapsible tube, a water swellable base member that surrounds all but one end of the tube, and an optional water permeable skin around the base member. The dispenser operates by the member absorbing water and expanding, which expansion squeezes the collapsible tube causing its contents to be expelled from the free end of the tube. In U.S. Pat. No. 3,987,760, Eckenhoff et al., discloses an improved osmotic dispenser for delivering agents. The dispenser consists of a layer of an osmotically effective solute positioned between a bag and a semipermeable wall. The improvement relates to a conduit for filling the bag. The dispenser operates by solute imbibing fluid into the dispenser, which fluid generates hydraulic pressure that is applied against the bag, causing it to squeeze inwardly forcing agent from the dispenser. In U.S. Pat. No. 3,971,376, Wichterle discloses a dispenser for delivering an agent, which dispenser consists of a capsule having unitary walls formed of a gel material swellable in fluids. A textile fabric is imbedded in the material for imparting strength and minimizing problems due to poor mechanical properties associated with the material that occurs during fluid uptake used to power the dispenser. Another dispenser is disclosed in U.S. Pat. No. 3,995,631 by Higuchi et al. The dispenser in this patent comprises a bag bearing on its outer surface a layer of an osmotic solute, and an outer wall formed of a material having in at least a part controlled permeability to fluid. In operation, the dispenser imbibes fluid and forms a solution of the solute, which solution squeezes the bag and thusly delivers agent from the dispenser. In copending U.S. patent application Ser. No. 06/115,750 and now U.S. Pat. No. 4,304,232 issued on Dec. 8, 1981, applicant Michaels discloses a dispenser comprising a wall that governs the passage of fluid into the dispenser, a container that can change in volume and has a passageway dimensioned for controlling the rate of release from the container, and a lamina formed of a material that absorbs fluid and is positioned between the wall and the container. The dispenser delivers agent by the combined operations of the wall, the lamina, the container, and the passageway acting together for urging the agent from the dispenser.

While the above dispensers are useful for delivering numerous agents to many environments of use, and while the dispensers represent a major advancement in the dispensing art, it will be appreciated by those versed in the art, there are instances where a dispenser made with an inventively novel improvement would also enjoy a wise use and application in the dispensing art. For example, if a dispenser is made from a wall forming material that combines both semipermeable and hydrophilic properties into a single material suitable for powering the dispenser, thereby providing an improvement in the dispenser, by advancing the structural property and enhancing the operability of the dispenser, while simultaneously reducing the number of steps needed to make the dispenser, such a dispenser would have immediate acceptance, and it also would represent a valuable contribution in the fields of science and commerce.

OBJECTS OF THE INVENTION

Accordingly, it is an immediate object of this invention to provide a novel dispenser for delivering fluids and beneficial agents to environments of use, and which dispenser represents an improvement in the dispenser art.

Yet another object of the invention is to provide a dispenser comprising a wall that imparts structure and shape to the dispenser and which wall is also a potential source of energy for powering the dispenser.

Still another object of the invention is to provide a dispenser that is self-powered in fluid environments, is easy to manufacture, and can be used for dispensing beneficial agents to animals, including humans, and to other biological and non-biological environments of use.

Yet still another object of the invention is to provide a dispenser comprising a wall for admitting and absorbing fluid, and which retains a significant fraction of the fluid for increasing its dimensions, which increase can be used as an expanding force for delivering an agent from the dispenser.

Another object of the invention is to provide a dispenser that is empty until filled, and when filled can administer a complete pharmaceutical dosage regimen for a period of time, the use of which requires intervention only for the initiation and the termination of the regimen.

Another object of the invention is to provide a dispenser fabricated with a wall that can function in a plurality of fluid environments.

It is a further object of the invention to provide a novel dispenser, which can operate to yield results substantially equivalent to those obtained with sustained release methods of drug administration.

Other objects, features and advantages of the invention will be apparent to those skilled in the art, from the detailed description of the specification, taken in conjunction with the drawings, and the accompanying claims.

SUMMARY OF THE INVENTION

The invention concerns a dispenser for delivering a fluid or an agent to an environment of use. The dispenser in a presently preferred embodiment is manufactured as a dispensing device especially designed for dispensing drug to a biological environment. The dispenser comprises a wall formed of a semipermeable polymer having a hydrophilic, fluid absorbing polymer grafted thereto. The wall surrounds an inner collapsible container made of an elastomeric material, which container houses a useful agent or a fluid. In operation, the dispenser releases the agent or fluid in response to the wall admitting and absorbing fluid from the environment and expanding, thereby exerting pressure on the container which collapses under pressure and ejects the agent or the fluid from the dispenser.

BRIEF DESCRIPTION OF THE DRAWINGS

In the drawings, which are not drawn to scale, but are set-forth to illustrate various embodiments of the invention, the figures are as follows.

In the drawings and the specification, like parts in relating Figures are identified by like numbers. The terms appearing earlier in the specification, and in the description of the drawings, as well as embodiments thereof, are further described elsewhere in the disclosure.

DETAILED DESCRIPTION OF THE DRAWINGS

Figure 1:
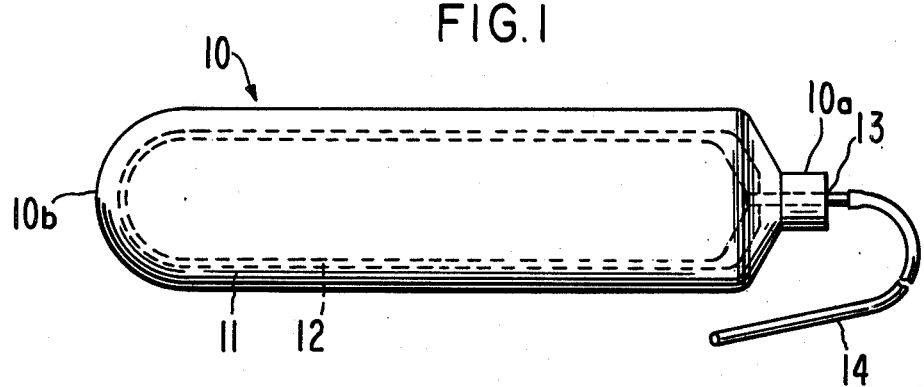
FIG. 1 is a side view illustrating a dispenser made according to the invention.

Turning now to the drawings in detail, which are an example of a new and useful dispenser for dispensing a fluid, or a fluid containing a useful agent, including drug, and which example is not to be construed as limiting, one dispenser is illustrated in FIG. 1 by the numeral 10. In FIG. 1, diispenser 10 has a lead end 10a and a rear end 10b, with dispenser 10 sized, shaped and adapted for placing and retaining dispenser 10 in an environment of use. Dispenser 10 comprises a wall 11, which wall is a housing that surrounds and defines an internal space, for housing a container 12, illustrated by a broken line. Container 12 has a passageway 13, which is an outlet means for dispensing a fluid or an agent from dispenser 10. A releasable tube 14 is provided for dispensing the contents of container 10 to a receiving site.

Figure 2:
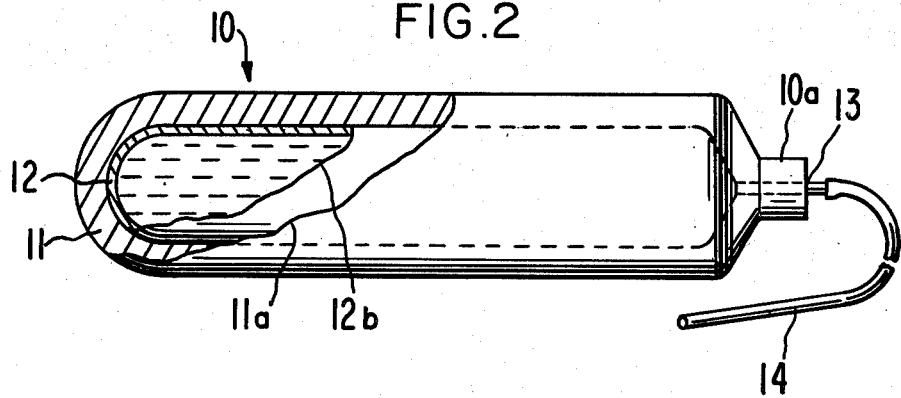
FIG. 2 illustrates the dispenser in opened-section with a portion of its wall and the wall of a container housed in the dispenser removed for illustrating the structural characteristics of the dispenser; and, FIG. 3 is a view similar to FIG. 2 illustrating the dispenser in operation delivering its contents.

FIG. 2 is a view of dispenser 10 with a section of wall 11 removed at 11a for depicting wall 11. FIG. 2 also shows container 12 having a section of container wall 12a opened for illustrating the structure of container 12. Wall 11 is made from a material that imparts physical integrity and support to dispenser 10 throughout the dispensing period, and it possesses the ability when activated by an exterior fluid to provide the driving force needed for operating dispenser 10. Wall 11 comprises structurally a semipermeable polymer modified by having grafted thereto a hydrophilic polymer, which wall 11 has the general formula:

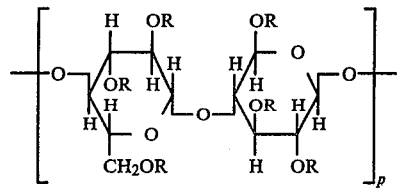

wherein R is a member selected from the group consisting of hydrogen, alkyl of 1 to 7 carbons, acetyl, propionyl, butyryl, valeryl, pivaloyl, and a hydrophilic chain of the general formula:

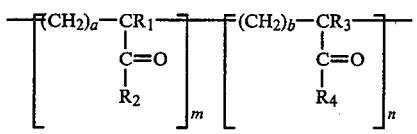

wherein $R_1$ and $R_3$ are the same or different and they are selected from the group consisting of hydrogen, alkyl of 1 to 7 carbon atoms and alkenyl of 2 to 4 carbon atoms, $R_2$ and $R_4$ are the same or different and they are selected from the group consisting of hydroxyl, —O-alkali metal, and —$NH_2$, a is 1 to 4, b is 0 to 4, p is 30 to 100,000, m is 0 to 5000, n is 0 to 5000 with the total of m plus n at least 500, and at least one of said R is the hydrophilic chain.

The cellulosic semipermeable backbone comprising the structure include presently preferred members such as cellulose, cellulose monacylate, cellulose monopropionate, cellulose butyrate and the like. The hydrophilic chains include the presently preferred members selected from the group consisting of polyacrylic acid, alkali polyacrylate such as sodium or potassium acrylate, and copolymers of these obtained by hydrolysis of polyacrylonitrile chains. The hydrophilic members are polymers of an olefinically unsaturated carboxylic acid or a derivative thereof with itself or with at least one other monomer. The resulting polycarboxylic acid polymers can include monomer units such as acrylic acid, acrylic anhydride, methacrylic acid, crotonic acid, maleic acid, itaconic acid, citraconic acid, alpha-dimethyl maleic acid, alpha-butyl maleic acid, fumaric acid, aconitic acid, including partial salts, amides and esters thereof, and the like.

The hydrophilic polymer is grafted onto the cellulosic polymer backbone in one embodiment through free radical mechanism. In this embodiment a free radical is positioned on the cellulosic polymer which serves as a reducing agent, with the hydrophilic polymer attaching to the cellulosic reducing agent through a carbon bond to yield a graft copolymer comprising the semipermeable polymer-hydrophilic polymer. Grafting of the hydrophilic polymer onto the cellulose polymer is carried out simultaneously with the formation of the hydrophilic polymer in a reaction medium such as an aqueous medium. In this preparation, the peroxide catalyst used to copolymerize the monomers form a redox catalyst in combination with a reducing agent, and it also serves to effect hydrophilic polymer bonding onto the cellulose polymer. Suitable reducing agents for the present purpose are cerous ion, ferrous ion, cobaltous ion, cuprous ion and the like. The ions can be used in forms of their salts such as ceric ammonium nitrate, ferrous ammonium sulfate, and the like. The graft copolymerization of olefinically unsaturated hydrophilic polymers onto the cellulosic polymer can also be carried out by irradiation such as ultraviolet, gamma or X-radiation, and the like. Procedures for preparing the grafted copolymer are disclosed in U.S. Pat. No. 4,105,033. Generally, wall 11 will have a thickness of from 0.1 mm to 8 mm, or more.

Figure 3:
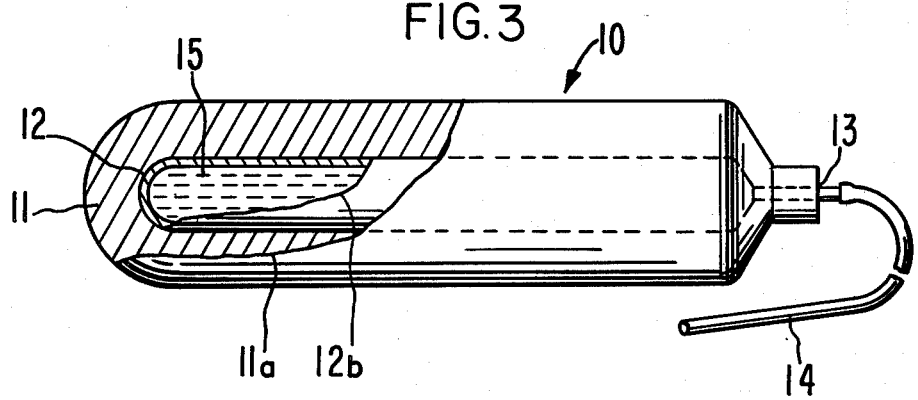

FIG. 3 is a view of dispenser 10 seen in opened-section for illustrating the operation of the dispenser. FIG. 3 illustrates container 12, also seen in opened-section, and housing ingredient 15, which may be a fluid, a beneficial agent, a composition or the like. Container 12 is made from a material that can house the ingredients free from any adverse effects on the contents of container 12. The container can also house its contents over a prolonged period of time sheltered from any possible adverse action produced by contacting the environment of use. Container 12 has a passageway 13 that is preferably formed during manufacture of container 12, and it has internal dimensions that assist in governing the rate of release of its contents from container 12. In operation wall 11 admits fluid into dispenser 10 and retains the fluid, and consequently expands from a position seen in FIG. 2 to the position seen in FIG. 3. This expansion is applied as a force against container 12 causing it to decrease in size and expel its contents through passageway 13 to the exterior of dispenser 10.

Container 12 is made from an elastomeric, or other low-modulus material, that can decrease its dimensions over time, and more particularly, collapse in response to pressure applied against its exterior surface as wall 11 absorbs fluid, retains fluid and expands. Typical elastomeric polymers include natural rubber, [often identified by the synonyms poly(2-methyl-1,3-butadiene) and cis-1,4-polyisoprene], gutta percha or trans-polyisoprene, cyclized rubber, silicone rubber, synthetic isoprene rubber, butadiene rubber, copolymeric styrene-butadiene rubbers, nitrile rubber, chloroprene rubber, ethylene-propylene rubbers, butyl rubbers, and the like. These elastomeric materials are disclosed in *Handbook of Common Polymers*, by Scott and Roff, Sections 29 through 40, 1971, published by the Chemical Rubber Co., Cleveland, Ohio. Container 12, formed from the above representative materials, can have a wall of varying thickness, usually about 0.001 mm to 7 mm, or more depending on the container, and the use of dispenser 10.

The contents that can be housed and delivered by dispenser 10 include fluids such as water, saline, buffer, plasma, and the like. Typical agents that can be delivered include algicides, anti-oxidants, air-purifiers, biocides, bactericides, catalysts, chemical reactants, cosmetics, disinfectants, drugs, fungicides, flavoring agents, foods, food supplements, fertility inhibitors, fermentation agents, fertility promoters, germicides, insecticides, micro-organism alternators, nutrients, pesticides, plant growth promoters, plant growth inhibitors, preservating agents, slimicides, surfactants, sterilization agents, sex sterilants, vitamins, and other like useful and beneficial agents that benefit animals including man, and the environment.

Exemplary drugs that can be administered according to the spirit of the invention include locally and systemically acting drugs. These drugs include a member selected from the group consisting of physiologically and pharmacologically acting drugs such as gastrointestinal administrable drugs, central nervous system acting drugs, hypnotic, sedative, psychic energizer, tranquilizer, anticonvulsant, antiparkinson, muscle relaxant, analgesic, antipyretic, antiinflammatory, anesthetic, antispasmodic, antimicrobial, antiviral, antiulcer, hormonal, sympathomimetic, diuretic, hypoglycemic, vitamins, contraceptive and ophthalmic drugs. These beneficial drugs and their dose amounts for humans are known to the art in *Drill's Pharmacology in Medicine*, edited by DiPalma, 1965, published by McGraw Hill Book Company, New York, in *Pharmacological Basis of Therapeutics*, by Goodman and Gilman, 4th Ed., 1970, published by MacMillan Co., London, and in U.S. Pat. No. 3,977,404. The drug in the container can be mixed with a pharmaceutically acceptable liquid such as water, saline, cottonseed oil, sesame oil, ethylene oleate, isopropyl myristate, propylene glycol, and the like. The drug can be present in solution, in semi-solid or paste formulation, in a thixotropic state, and the like. Pharmaceutically acceptable carriers and the like are known to the dispensing art in *Remington's Pharmaceutical Science*, 14th Ed., pages 1461–1477, 1970, published by the Mack Publishing Co., Easton, PA.

An improved dispenser is manufactured by following the specification as follows: first, a cylindrical shaped container 4.0 cm long, 3.8 mm inside diameter and 4.8 mm ouside diameter, is injection molded at 180° C., at 77–84 kg/cm$^2$, from an elastomeric copolymer styrene-butadiene. Next, an expandable-collapsible mandrel is inserted into the container, and the assembly suspended in one section of a two-piece cavity mold while providing a space between the assembly and the mold. Then, the mold is charged with an aqueous slurry of cellulose which is overlayed with a monomer mixture of 30% ethylene glycol monomethacrylate, 1% bis-methacrylate and 69% of a 10% solution of ammonium persulfate in distilled water. The assembly is then heated to about 60° C. and placed in a carbon dioxide environment, with polymerization and entrapment of the hydrophilic polymer in the semipermeable polymer completed in about 15 minutes. The mold is then cooled, the procedure repeated for the other section of the mold, the mold cooled and removed at room temperature, to yield the dispenser.

In another embodiment the wall can be formed as a pair of molds having when joined dimensions corresponding to the total exterior dimensions of the container. In this embodiment, the molds are first charged with a layer of polymeric wall forming cellulose to which is added the monomer methacrylic acid, a peroxide catalyst and the reducing agent ferrous ammonium sulfate to form a hydrophilic copolymer having chains thereof physically entrapped into the network of the cellulosic polymer during the polymerization process. Procedures for practicing the process are disclosed in U.S. Pat. Nos. 3,256,372 and 4,105,033. Then, the wall is removed from the molds, placed around a container, and their surfaces joined by adhesive bonding to yield a strong wall. The adhesives that can be used include glues, starches, oxidized starches, chlorinated starches, natural rubber-based adhesives, styrene-butadiene rubber adhesive, nitrile rubber adhesive, phenolic adhesive, amino resin adhesives, silicone rubber adhesives, epoxy resin adhesives, acrylic ester adhesives, and the like. Suitable adhesives and procedures for using adhesives are disclosed in *Adhesion and Bonding* by Norbet M. Mikales, 1971, published by Wiley-Interscience, New York.

The wall of dispenser 10 can also comprise cellulose acylate having one degree of substitution grafted with hydrophilic chains of polymerized methacrylic acid, cellulose acylate having one degree of substitution grafted with hydrophilic chains of polymerized methacrylamide, grafted cellulose having hydrophilic chains consisting of polyacrylamide-sodium polyacrylate copolymer, cellulose having hydrophilic chains of polyacrylic acid-sodium polyacrylate copolymer, cellulose having grafted thereto copolymeric ethylene glycol monoethacrylate and ethylene glycol bis-methacrylate, and the like.

The containers in the above embodiments can be charged with saline, or tetracycline hydrochloride in polyethylene glycol 200, or epinephrine hydrochloride in buffer, for delivery to a receptor site. And, while the above presentation is illustrative of various dispensers that can be provided by the invention, it is to be understood these dispensers are not to be construed as limiting, as they can take a wide variety of shapes, sizes and forms adapted for delivering a fluid, an agent, or a mixture thereof. For example, the dispenser can be manufactured for dispensing drug to animals, which term includes warm-blooded mammals, humans, sport, farm and zoo animals. The dispenser can be used for dispensing drugs to avians, pices and reptiles. The dispenser can be sized, shaped, and adapted for dispensing drugs to body cavities, body openings, for oral administration, for use as intramuscular implants, intrauterine, vaginal, cervical, rectal, nasal, ear, ocular, and dermal applications. The dispenser can also be used as an artificial gland, and arterial and venous administration of drugs. The dispenser can be used in commerce broadly including in homes, hospitals, nursing homes, ships, laboratories, factories, and the like.

Although the foregoing has been described in details by way of illustration of presently preferred embodiments for the purpose of clarity of understanding, it will be understood that certain changes and modifications may be practiced without departing from the scope and spirit of the invention.

I claim:

1. A dispenser comprising: an outer wall formed of a semi-permeable polymer onto which is grafted a hydrophilic polymer, the semi-permeable polymer comprising the general formula:

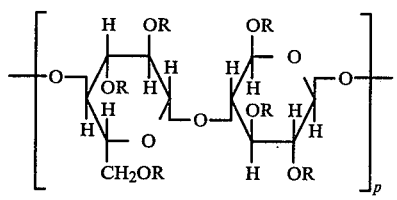

wherein R is a member selected from the group consisting of hydrogen, alkyl of 1 to 7 carbon atoms, acetyl, propionyl, butyryl, valeryl, pivaloyl, and the hydrophilic polymer comprising the general formula:

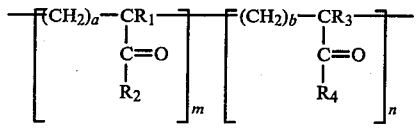

wherein $R_1$ and $R_3$ are a member selected from the group consisting of hydrogen, alkyl of 1 to 7 carbon atoms, and alkenyl of 2 to 4 carbon atoms, $R_2$ and $R_4$ are a member selected from the group consisting of hydroxyl, —O-alkali metal and $NH_2$, a is 1 to 4, b is 0 to 4, p is 30 to 100,000, m is 0 to 5000, n is 0 to 5000 with the total of m plus n at least 500, and at least one of said R is the hydrophilic member, which wall surrounds and defines an internal space; a container for storing a member selected from the group consisting of a fluid and a beneficial agent in the internal space, the container formed of an elastomeric polymer that is changeable from a storing capacity to a substantially emptied capacity over time; an outlet passageway in the wall communicating with the container and the exterior of the dispenser for dispensing the stored member over time; and wherein when the dispenser is in operation in the environment of use, the dispenser releases the beneficial member in response to the wall admitting and absorbing fluid from the environment and expanding, thereby exerting pressure on the container which collapses under the pressure and ejects the member through the passageway from the dispenser over time.

2. The dispenser of claim 1, wherein the beneficial agent is a drug, which drug is present in solution, in semi-solid, or in thixotropic formulation.

3. The dispenser of claim 1, wherein the dispenser is sized, shaped, and adapted for oral use.

4. The dispenser of claim 1, wherein the dispenser is sized, shaped and adapted for vaginal use.

5. The dispenser of claim 1, wherein the dispenser is sized, shaped and adapted for ano-rectal use.

6. The dispenser of claim 1, wherein the dispenser is sized, shaped and adapted for use as an implant.

7. The dispenser of claim 1, wherein the container is made of a member selected from the group consisting of natural rubber, gutta percha, cyclized rubber, silicone rubber, isoprene rubber, butadiene rubber, styrene-butadiene rubber, nitrile rubber, chloroprene rubber, ethylene-butylene rubber, and butyl rubber.

8. The dispenser of claim 1, wherein the container is connected to a conduit leading to a distant site.

9. The dispenser of claim 1, wherein the container contains a member selected from the group consisting of an algicide, antioxidant, air-purifier, food suppliment, and plant growth hormone.

10. The dispenser of claim 1, wherein the wall is formed of two sections adhesively bonded together with an adhesive which is a member selected from the group consisting essentially of glues, polyamides, starches, oxidized starches, chlorinated starches, natural rubber, nitrile, neoprene, styrene-butadiene, phenolic, amino resin, silicone rubber, acrylic, cyanoacrylic, and epoxy adhesives.

* * * * *